United States Patent [19]

Nakai et al.

[11] Patent Number: 5,206,428
[45] Date of Patent: Apr. 27, 1993

[54] TETRAHYDRONAPHTHALENE DERIVATIVES AND PREPARATION THEREOF

[75] Inventors: Hideo Nakai, Takarazuka; Toyoharu Yamashita, Ageo; Harumichi Kohno; Yasuhiko Sasaki, both of Urawa; Akio Odawara, Tokyo, all of Japan

[73] Assignee: Tanabe Seiyaku Co., Ltd., Osaka, Japan

[21] Appl. No.: 605,433

[22] Filed: Oct. 30, 1990

[30] Foreign Application Priority Data

Nov. 16, 1989 [JP] Japan .................. 1-297878

[51] Int. Cl.⁵ ............................ C07C 317/26
[52] U.S. Cl. ...................... 562/427; 560/10; 564/92
[58] Field of Search ........... 562/427, 430; 560/10, 560/13; 514/562, 510, 604; 564/92

[56] References Cited

U.S. PATENT DOCUMENTS 4,868,331 9/1989 Niewöhner et al. ............ 562/427
4,868,332 9/1989 Niewöhner et al. ............ 560/10
4,886,898 12/1989 Niewöhner et al. ............ 562/451

FOREIGN PATENT DOCUMENTS 0317321 5/1989 European Pat. Off. .
0330380 8/1989 European Pat. Off. .
0430459 11/1989 European Pat. Off. ............ 564/92

OTHER PUBLICATIONS

Hanasaki et al., Biochem. Pharmac., vol. 38, No. 12, pp. 2007-2017 (1989).
Bush et al, Thrombosis Research, vol. 44, pp. 377-389 (1986).
Lumley et al, Br. J. Pharmac., vol. 97, pp. 783-794 (1989).

Primary Examiner—José G. Dees
Assistant Examiner—B. Frazier
Attorney, Agent, or Firm—Birch, Stewart, Kolasch & Birch

[57] ABSTRACT

A tetrahydronaphthalene derivative of the formula:

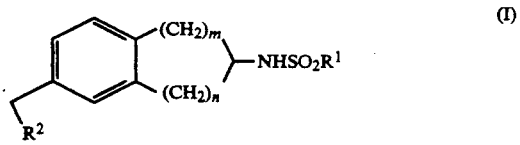

(I)

wherein $R^1$ is a substituted or unsubstituted phenyl group, naphthyl group, a sulfur- or nitrogen-containing heterocyclic group, a lower alkyl group or cycloalkyl group, and $R^2$ is hydroxymethyl group, carboxyl group, a lower alkoxycarbonyl group or a group of the formula:

$$-CO-N(R^3)-R^4$$

wherein $R^3$ is hydrogen atom or a lower alkyl group, $R^4$ is a lower alkoxycarbonyl-phenyl group, carboxyphenyl group, a lower alkyl group, a lower alkoxycarbonyl-lower alkyl group or carboxy-lower alkyl group, and m and n are different and are 1 or 2, or a pharmaceutically acceptable salt thereof, which are useful as a platelet aggregation-inhibiting agent and as an agent for the treatment, amelioration and/or prophylaxis of a variety of thrombosis or embolism, coronary and cerebral vascular smooth muscle vellication, asthma, and the like, processes for the preparation thereof, and pharmaceutical composition containing said compound as an active ingredient.

10 Claims, No Drawings

TETRAHYDRONAPHTHALENE DERIVATIVES AND PREPARATION THEREOF

FIELD OF THE INVENTION

This invention relates to novel tetrahydronaphthalene derivatives, processes for preparation thereof and intermediates therefor.

PRIOR ART

Thromboxan $A_2$ (hereinafter, referred to as "$TxA_2$") is a metabolite of arachidonic acid which exists widely in various organs of animals (e.g. liver, kidney, lung, brain, etc.). Said $TxA_2$ is known to show platelet aggregation activity and induces a variety of thrombosis such as peripheral vascular thrombosis, pulmonary embolism, coronary artery thrombosis, myocardial infarction, transient ischemia, and the like. Therefore, 2-benzenesulfonylaminoethyl derivatives of phenoxyacetic acid or tetrahydronaphthyloxyacetic acid which have $TxA_2$-antagonistic activity have been suggested to be useful for therapeutic treatment of these diseases (cf. Thrombosis Research, 35, 379-395, 1984, U.S. Pat. No. 4,868,331).

SUMMARY DESCRIPTION OF THE INVENTION

As a result of various investigation, there has been found novel tetrahydronaphthalene derivatives which show stronger $TxA_2$ antagonistic activity as compared with the above known compounds.

Thus, the objects of the invention are to provide novel tetrahydronaphthalene derivatives and a pharmaceutical composition containing the same. Another object of the invention is to provide processes for preparing said compounds. A further object of the invention is to provide novel intermediates which are useful in the synthesis of the tetrahydronaphthalene derivatives of the invention. These and other objects and advantages of the invention will be apparent to those skilled in the art from the following description.

DETAILED DESCRIPTION OF THE INVENTION

This invention relates to a tetrahydronaphthalene derivative of the formula:

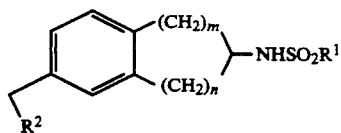
(I)

wherein $R^1$ is a substituted or unsubstituted phenyl group, naphthyl group, a sulfur- or nitrogen-containing heterocyclic group, a lower alkyl group or cycloalkyl group, and $R^2$ is hydroxymethyl group, carboxyl group, a lower alkoxycarbonyl group or a group of the formula:

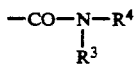

wherein $R^3$ is hydrogen atom or a lower alkyl group, $R^4$ is a lower alkoxycarbonyl-phenyl group, carboxyphenyl group, a lower alkyl group, a lower alkoxycarbonyl-lower alkyl group or carboxy-lower alkyl group, and m and n are different and are integers of 1 and 2, or a pharmaceutically acceptable salt thereof.

Said tetrahydronaphthalene derivative of the invention and a salt thereof show potent $TxA_2$ antagonistic and/or platelet aggregation-inhibiting activities and are useful for the therapeutic treatment, amelioration and/or prophylaxis of a variety of thrombosis or embolism, coronary and cerebral vascular smooth muscle vellication, asthma, and the like.

Examples of the novel tetrahydronaphthalene derivative of the invention are those of the formula (I) wherein $R_1$ is phenyl group, a lower alkylphenyl group, a lower alkoxyphenyl group, a halogenophenyl group, naphthyl group, thienyl group, pyridyl group, a lower alkyl group or cycloalkyl group.

Among them, preferred examples of the compound of the invention are those of the formula (I) wherein $R^2$ is hydroxymethyl group, carboxyl group, or a group of the formula:

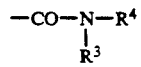

wherein $R^3$ is hydrogen atom and $R^4$ is carboxy-lower alkyl group.

Another preferred examples of the compound of the invention are those of the formula (I) wherein m is 1 and n is 2.

More preferred examples of the compound of the invention are those of the formula (I) wherin $R^1$ is phenyl group, methylphenyl group, methoxyphenyl group, chlorophenyl group, thienyl group, methyl group or cyclohexyl group, and $R^2$ is carboxyl group or a group of the formula:

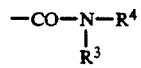

wherein $R^3$ is hydrogen atom and $R^4$ is a carboxy-lower alkyl group.

Most preferred examples of the compounds of the invention are those of the formula (I) wherein $R^1$ is chlorophenyl group, and $R^2$ is a group of the formula:

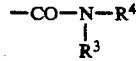

wherein $R^3$ is hydrogen atom and $R^4$ is carboxyethyl group or carboxypropyl group.

In the above-mentioned examples of the tetrahydronaphthalene derivative (I), the lower alkyl group, the lower alkoxy group and the cycloalkyl group include an alkyl group of one to six carbon atoms, an alkoxy group of one to six carbon atoms and cycloalkyl group of three to six carbon atoms, respectively. Preferred examples of these groups are an alkyl group of one to four carbon atoms, an alkoxy group of one to four carbon atoms and cycloalkyl group of five to six carbon atoms, respectively. Examples of the sulfur- or nitrogen-containing heterocyclic group are sulfur- or nitrogen-containing 5- or 6-membered heteromonocyclic groups such as thienyl or pyridyl groups.

The compounds (I) of the invention may exist in the form of two optically active isomers due to one asymmetric carbon atom, and this invention includes these optically active isomers and a mixture thereof.

According to this invention, the compound (I) or salts thereof can be prepared by condensing an aminotetrahydronaphthalene derivative of the formula:

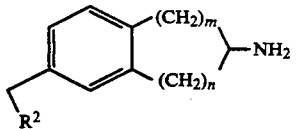

wherein $R^2$, m and n are as defined above, or a salt thereof with a sulfonic acid compound of the formula:

   (III)

wherein $R^1$ is as defined above, or a reactive derivative thereof.

The compound of the formula (I) wherein $R^2$ is hydroxymethyl group, i.e. the compounds of the formula (I-a):

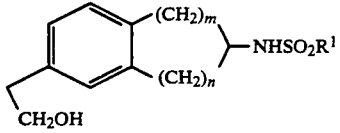

wherein $R^1$, m and n are as defined above, can also be prepared by reducing a compound of the formula (I-b):

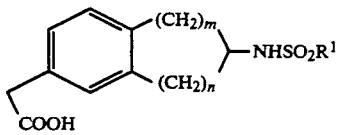

wherein $R^1$, m and n are as defined above.

On the other hand, the compounds of the formula (I) wherein $R^2$ is a group of the formula:

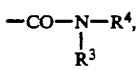

i.e. the compounds of the formula (I-c):

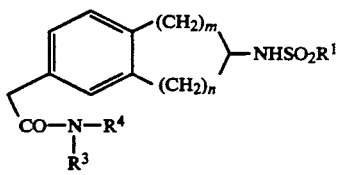

wherein $R^1$, $R^3$, $R^4$, m and n are as defined above may be prepared by condensing a compound of the formula (I-b) or a reactive derivative at carboxyl group thereof with an amine compound of the formula:

   (IV)

wherein $R^3$ and $R^4$ are as defined above, or a salt thereof.

Moreover, the compounds of the formula (I) wherein $R^2$ is a group of the formula:

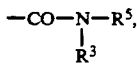

i.e. the compounds of the formula (I-d):

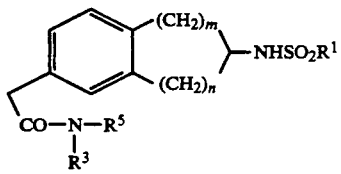

wherein $R^5$ is carboxy-phenyl group or a carboxy-lower alkyl group, and $R^1$, $R^3$, m and n are as defined above, may be prepared by hydrolyzing a compound of the formula (I-e):

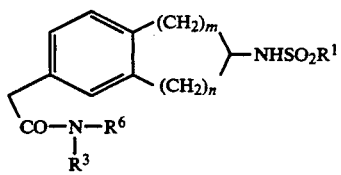

wherein $R^6$ is a lower alkoxycarbonyl-phenyl group or a lower alkoxycarbonyl-lower alkyl group, and $R^1$, $R^3$, m and n are as defined above.

The condensation reaction of the aminotetrahydronaphthalene (II) or a salt thereof with the sulfonic acid compound (III) or a reactive derivative thereof can be carried out in the presence or absence of an acid acceptor. The reactive derivative of the compound (III) includes any conventional reactive derivatives, for example, the corresponding sulfonyl halide. The acid acceptor includes any conventional agents, for example, alkali metal carbonates, alkali metal hydrogen carbonates, trialkylamines, pyridine, and the like. Examples of the salt of the starting compound (II) include mineral acid salts (e.g., hydrochloride, sulfate, etc.), organic acid salts (e.g., methanesulfonate, p-toluenesulfonate, dibenzoyltartrate etc.), and so forth. The reaction is preferably carried out in a suitable solvent (e.g. water, ethyl acetate) at a temperature of 0° to 200° C.

The reduction of the compound (I-b) can be carried out by treating it with a reducing agent. The reducing agent includes, for example, borane 1,4-oxathiane complex. This reduction is preferably carried out in an appropriate solvent (e.g. ether tetrahydrofuran) at a temperature of 0° to 50° C.

The condensation reaction of the compound (I-b) or a reactive derivative at carboxyl group thereof with the amine compound (IV) can be carried out by any conventional method. For example, the condensation reaction of the free carboxylic acid (I-b) and the compound (IV) can be carried out in the presence of a dehydrating agent. The dehydrating agent includes, for example, carbonyldiimidazole, dicyclohexylcarbodiimide, and the like. Besides, the condensation reaction of the reactive derivative at carboxyl group of the compound (I-b)

with the amine compound (IV) can be carried out in the presence or absence of an acid acceptor. A variety of the reactive derivative at the carboxyl group of the compound (I-b), including, for example, acid halides, activated esters may be used for the condensation reaction. The acid acceptor includes alkali metal carbonates, alkali metal hydrogen carbonates, trialkylamines, pyridine, and the like. These reactions are preferably carried out in an appropriate solvent (e.g. tetrahydrofuran, methylene chloride, ethyl acetate) at a temperature of 0° to 50° C.

The hydrolysis of the compound (I-e) can be carried out by conventional method, for example, by treating the compound with an alkali agent or an acid. Examples of the alkali agent are alkali metal hydroxides, and examples of the acid are mineral acids. The hydrolysis is preferably carried out in an appropriate solvent (e.g. water, a lower alkanol) at a temperature of 0° to 30° C.

All of the above reactions proceed without racemization, and hence, when an optically active compounds are used as the starting compounds, the desired compounds (I) can be obtained in the optically active form.

The compounds (I) of this invention can be used for pharmaceutical use either in the free form or a pharmaceutically acceptable salt. Examples of the pharmaceutically acceptable salts include inorganic or organic salts such as alkali metal salts (e.g. sodium salt, potassium salt), alkaline earth metal salts (e.g. calcium salt, magnesium salt), heavy metal salts (e.g. zinc salt), ammonium salt, organic amine salts (e.g. triethylamine salt, pyridine salt, ethanolamine salt, a basic amino acid salt), and the like. These salts may readily be prepared by treating the compounds (I) with the corresponding inorganic or organic base in an appropriate solvent.

The compounds (I) or a salt thereof may be administered either orally or parenterally to a warm-blooded animal, including human beings, and may also be used in the form of a pharmaceutical preparation containing the same compound in admixture with pharmaceutical excipients suitable for oral or parenteral administration. The pharmaceutical preparations may be in solid form such as tablets, capsules and powders, or in liquid form such as solutions, suspensions or emulsions. Moreover, when administered parenterally, it may be used in the form of injections.

Because of the potent TxA$_2$ antagonistic activity, the compound (I) of the invention or a salt thereof are useful as platelet aggregation-inhibiting agent and for the treatment, amelioration and/or prophylaxis of a variety of thrombosis or embolism, such as cerebral thrombosis, coronary artery thrombosis, pulmonary thrombosis, pulmonary embolism, peripheral vascular embolism, thromboangiitis, and the like. The compound (I) or a salt thereof are also useful for prophylaxis of i) thrombosis which may be caused during extracorporeal circulation of blood and ii) thrombosis in case of an organ transplantation.

Moreover, based on the potent TxA$_2$ antagonistic activity, the compound (I) or a salt thereof may be used for the treatment, amelioration and/or prophylaxis of myocardial ischemia, unstable angina pectoris, coronary vellication, cerebral blood vessel vellication after subarachnoid hemorrhage, cerebral hemorrhage, asthma, nephritis, renal failure, a shock, and the like. Besides, as some known TxA$_2$ antagonists shown excellent TxA$_2$ antagonistic activity but at the same time show transient TxA$_2$-like activity, they are liable to side effects such as platelet aggregation-inducing activity, broncho-constriction activity, blood vessel constriction activity. As compared with the known antagonists, however, the compound (I) of this invention is quite advantageous for use by either oral or parenteral administration because it is substantially free from such TxA$_2$-like activity.

Concomitantly, the starting compound (II) wherein m is 1 and R$^2$ is a lower alkoxycarbonyl group can be prepared, for example, by the steps of reacting an acid chloride of mono(a lower alkyl) 1,4-phenylenediacetic acid with ethylene to give a lower alkyl 6-oxo-5,6,7,8-tetrahydronaphthalene-2-acetate, and reacting the product with methoxylamine to give ethyl 6-methoxyimino-5,6,7,8-tetrahydronaphthalene-2-acetate (V), followed by a catalytic reduction.

On the other hand, the starting compound (II) wherein m is 2 and R$^2$ is a lower alkoxycarbonyl group can be prepared, for example, by hydrolysis of ethyl 7-methoxycarbonylamino-5,6,7,8-tetrahydronaphthalene-2-acetate, followed by treating the product with a lower alkanol.

The starting compound (II) wherein R$^2$ is carboxyl group can be prepared, for example, by hydrolysis of the corresponding compound (II) wherein R$^2$ is a lower alkoxycarbonyl group, and may be, if required, further condensed with the amine compound (IV) to give the compound (II) wherein R$^2$ is a group of the formula:

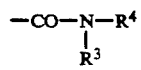

wherein R$^3$ and R$^4$ are as defined above.

The compound (II) wherein R$^2$ is hydroxymethyl group can be prepared by reducing the compound (II) wherein R$^2$ is carboxyl group or a lower alkoxycarbonyl group or by reducing the compound (V) by using borane methylsulfide complex.

EXPERIMENT

Effect on U-46619-induced platelet aggregation (in vitro)

Nine volumes of blood collected from a healthy human were mixed with one volume of 3.8% (w/v) trisodium citrate solution, and the mixture was centrifuged to give platelet-rich plasma ("PRP") as the supernatant. The bottom layer was further centrifuged to give platelet-poor plasma ("PPP") as the supernatant. PRP was diluted with PPP so that the platelet count was 4×10$^5$ cells/mm$^3$. 25 μl of a test compound solution was added to 200 μl of said diluted PRP. After the mixture was stirred for 2 minutes at 37° C., U-46619 solution (0.2 μg/ml solution) was added thereto to induce platelet aggregation. The degree of platelet aggregation was examined by Born's method (Nature, 194, 927 (1962)), and the platelet aggregation-inhibiting activity of the test compound was estimated. The platelet aggregation-inhibiting activity of the test compound was expressed as IC$_{50}$, i.e., the concentration of the test compound required to induce 50% inhibition of U-46619-induced platelet aggregation. The results are shown in the following Table 1.

TABLE 1

U-46619-induced platelet aggregation-inhibiting activity (in vitro)

| Test Compounds* | IC$_{50}$ (μg/ml) |
|---|---|
| (the compounds of the present invention) | |
| Compound No. 1 | 0.2 |
| Compound No. 2 | 0.06 |
| Compound No. 3 | 0.7 |

*)note: chemical name of each test compound:
Compound No. 1 Sodium 3-{[6-(4-methylphenyl)sulfonylamino-5,6,7,8-tetrahydronaphthalene-2-yl]acetylamino}-n-propionate
Compound No. 2 Sodium 6-(4-chlorophenyl)sulfonylamino-5,6,7,8-tetrahydronaphthalene-2-acetate
Compound No. 3 Sodium 4-{[6-(4-chlorophenyl)sulfonylamino-5,6,7,8-tetrahydronaphthalene-2-yl]acetylamino}-n-butyrate

EXAMPLE 1

A solution of 1.94 g of 4-chlorophenylsulfonyl chloride in 20 ml of ethyl acetate is added to a mixture of 30 ml of ethyl acetate, 20 ml of water, 3.46 g of potassium carbonate and 2.25 g of ethyl 6-amino-5,6,7,8-tetrahydronaphthalene-2-acetate hydrochloride under stirring at room temperature. After the mixture is stirred at room temperature for 45 minutes, the organic layer is separated therefrom, washed, dried and evaporated to remove the solvent. The residue is purified by silica gel column chromatography (solvent; chloroform) to give 2.84 g of ethyl 6-(4-chlorophenyl)sulfonylamino-5,6,7,8-tetrahydronaphthalene-2-acetate as oil.

Yield 83%

Mass(m/z): 408 (M$^+$+1).

IR$\nu_{max}^{neat}$(cm$^{-1}$): 3280, 1730, 1160.

EXAMPLES 2 to 15

The corresponding starting compounds are treated in the same manner as described in Example 1 to give the compounds shown in Tables 2 to 4.

TABLE 2

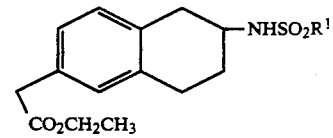

| Ex. No. | R$^1$ | Physical properties |
|---|---|---|
| 2 | phenyl | oil<br>MS(m/z): 374(M$^+$+1)<br>IR $\nu_{max}^{neat}$ cm$^{-1}$: 3270, 1730, 1160 |
| 3 | 4-CH$_3$-phenyl | oil<br>MS(m/z): 388(M$^+$+1)<br>IR $\nu_{max}^{neat}$ cm$^{-1}$: 3270, 1730, 1160 |
| 4 | thienyl | oil<br>MS(m/z): 380(M$^+$+1)<br>IR $\nu_{max}^{neat}$ cm$^{-1}$: 3280, 1730, 1160 |
| 5 | cyclohexyl | oil<br>MS(m/z): 380(M$^+$+1)<br>IR $\nu_{max}^{neat}$ cm$^{-1}$: 3280, 1730, 1140 |
| 6 | —CH$_3$ | m.p. 108.5-110° C.*$^1$<br>MS(m/z): 311(M$^+$)<br>IR $\nu_{max}^{neat}$ cm$^{-1}$: 3260, 1740, 1150 |
| 7 | —(CH$_2$)$_3$CH$_3$ | oil<br>MS(m/z): 353(M$^+$)<br>IR $\nu_{max}^{neat}$ cm$^{-1}$: 3280, 1730, 1150 |

*$^1$recrystallized from ethyl acetate and n-hexane (same as in the following Examples)

TABLE 3

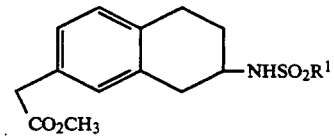

| Ex. No. | R$^1$ | Physical properties |
|---|---|---|
| 8 | 4-Cl-phenyl | oil<br>MS(m/z): 394(M$^+$+1)<br>IR $\nu_{max}^{neat}$ cm$^{-1}$: 3270, 1730, 1150 |
| 9 | 4-OCH$_3$-phenyl | oil<br>MS(m/z): 390(M$^+$+1)<br>IR $\nu_{max}^{neat}$ cm$^{-1}$: 3280, 1735 |
| 10 | naphthyl | oil<br>MS(m/z): 410(M$^+$+1)<br>IR $\nu_{max}^{neat}$ cm$^{-1}$: 3280, 1735 |
| 11 | pyridyl | oil<br>MS(m/z): 361(M$^+$+1)<br>IR $\nu_{max}^{neat}$ cm$^{-1}$: 3270, 1740 |
| 12 | —CH$_3$ | oil<br>MS(m/z): 298(M$^+$+1)<br>IR $\nu_{max}^{neat}$ cm$^{-1}$: 3280, 1735 |
| 13 | —(CH$_2$)$_3$CH$_3$ | oil<br>MS(m/z): 339(M$^+$+1)<br>IR $\nu_{max}^{neat}$ cm$^{-1}$: 3280, 1735 |

TABLE 4

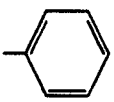

| Ex. No. | R¹ | Physical properties |
|---|---|---|
| 14 | 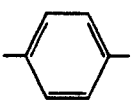 | colorless oil<br>MS(m/z): 332(M⁺ + 1)<br>IR $\nu_{max}^{neat}$ cm−1: 3500, 3280, 1160 |
| 15 | 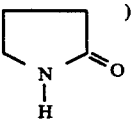 | colorless caramel<br>FABMS(m/z): 451(M⁺ + 1 + pyrrolidinone)<br>IR $\nu_{max}^{CHCl3}$ cm−1: 3380, 3270, 1335, 1160 |

EXAMPLE 16

(1) 8.29 g of potassium carbonate and 60 ml of ethyl acetate are added to 4.05 g of ethyl 6-amino-5,6,7,8-tetrahydronaphthalene-2-acetate hydrochloride, and 30 ml of water are added thereto under cooling and stirring. After the mixture is stirred at room temperature for 10 minutes, the organic layer is separated therefrom, dried and evaporated to remove the solvent to give 3.16 g of oil product. A solution of 5.64 g of (+)-D-dibenzoyltartaric acid in 50 ml of ethanol is added to a solution of the oil obtained above in 50 ml of ethanol. The precipitated crystals are collected and recrystallized from a mixture of ethanol and water to give 2.10 g of ethyl (+)-6-amino-5,6,7,8-tetrahydronaphthalene-2-acetate ½ (+)-D-dibenzoyltartrate as colorless prism.

Yield 34%.

m.p. 216°–217° C. (decomp.).

The mother liquid is evaporated to remove the solvent, and 30 ml of water, 8.29 g of potassium carbonate and 60 ml of ethyl acetate are added thereto. The organic layer is separated from the solution, dried and evaporated to remove the solvent to give 1.86 g of oil product. A solution of 3.32 g of (−)-L-dibenzoyltartaric acid in 50 ml of ethanol is added to a solution of the oil obtained above in 40 ml of ethanol. The precipitated crystals are collected and recrystallized from a mixture of ethanol and water to give 1.79 g of ethyl (−)-6-amino-5,6,7,8-tetrahydronaphthalene-2-acetate ½ (−)-L-dibenzoyltartrate as colorless prism.

Yield 29%.

m.p. 214°–215° C. (decomp.).

(2) 2.99 g of potassium carbonate, 20 ml of ethyl acetate and 40 ml of water are added to 2.09 g of ethyl (+)-6-amino-5,6,7,8-tetrahydronaphthalene-2-acetate ½ (+)-D-dibenzoyltartrate, and a solution of 1.28 g of 4-chlorophenylsulfonyl chloride in 20 ml of ethyl acetate is added thereto at room temperature under stirring. After the mixture is stirred at room temperature for 1.5 hour, the organic layer is separated therefrom, washed, dried and evaporated to revove the solvent. The residue is purified by silica gel column chromatography (solvent; chloroform) to give 2.10 g of ethyl (+)-6-(4-chlorophenyl)sulfonylamino-5,6,7,8-tetrahydronaphthalene-2-acetate as colorless viscous oil.

$[\alpha]_D^{20} + 44.6°$ (c=1.20, chloroform). Ethyl (−)-6-amino-5,6,7,8-tetrahydronaphthalene-2-acetate ½ (−)-L-dibenzoyltartrate is treated in the same manner as described above to give ethyl (−)-6-(4-chlorophenyl)sulfonylamino-5,6,7,8-tetrahydronaphthalene-2-acetate as colorless viscous oil.

$[\alpha]_D^{20} - 45.2°$ (c=1.47, chloroform).

EXAMPLE 17

28 ml of ethanol and 10 ml of a 2N aqueous sodium hydroxide solution are added to 2.81 g of ethyl 6-(4-chlorophenyl)sulfonylamino-5,6,7,8-tetrahydronaphthalene-2-acetate, and the mixture is stirred at room temperature overnight. After ethanol is removed from the mixture, water is added thereto, and the mixture is washed with methylene chloride. 10% hydrochloric acid is added to the water layer, and the mixture is extracted with ethyl acetate. The extract is washed, dried and evaporated to remove the solvent, and the residue is recrystallized from a mixture of ethyl acetate and n-hexane to give 2.16 g of 6-(4-chlorophenyl)sulfonylamino-5,6,7,8-tetrahydronaphthalene-2-acetic acid as pale brown prism.

Yield 82% m.p. 152°–154.5° C.

Mass(m/z): 380(M⁺ +1).

IR$\nu_{max}^{nujol}$(cm⁻¹): 3240, 1710, 1330, 1160.

Sodium salt: pale brown powder

FABMass(m/z): 424, 402(M⁺ +1).

IR$\nu_{max}^{nujol}$(cm⁻¹): 1580, 1380.

EXAMPLES 18 TO 31

The corresponding starting compounds are treated in the same manner as described in Example 17 to give the compounds shown in Table 5 to 6.

TABLE 5

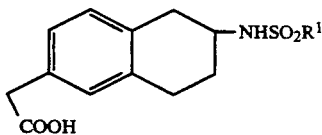

| Ex. No. | R¹ | Physical properties |
|---|---|---|
| 18 | phenyl | m.p. 127-128.5° C.*1<br>MS(m/z): 346(M+ + 1)<br>IR $\nu_{max}^{nujol}$ cm−1: 3300, 1700<br>Sodium salt: amorphous<br>FABMS(m/z): 390, 368(M+ + 1)<br>IR $\nu_{max}^{nujol}$ cm−1: 3260, 1570, 1460 |
| 19 | 4-methylphenyl | m.p. 160.5-162° C.*1<br>MS(m/z): 360(M+ + 1)<br>IR $\nu_{max}^{nujol}$ cm−1: 3280, 1700<br>Sodium salt: amorphous<br>FABMS(m/z): 404, 382(M+ + 1)<br>IR $\nu_{max}^{nujol}$ cm−1: 3260, 1570, 1460 |
| 20 | 2-thienyl | m.p. 143-145° C.*1<br>MS(m/z): 352(M+ + 1)<br>IR $\nu_{max}^{nujol}$ cm−1: 3290, 1700, 1330<br>Sodium salt: amorphous<br>FABMS(m/z): 396, 374(M+ + 1)<br>IR $\nu_{max}^{nujol}$ cm−1: 3260, 1570, 1380 |
| 21 | cyclohexyl | m.p. 163-164° C.*2<br>MS(m/z): 352(M+ + 1)<br>IR $\nu_{max}^{nujol}$ cm−1: 3280, 1690, 1320<br>Sodium salt: amorphous<br>FABMS(m/z): 396, 374(M+ + 1)<br>IR $\nu_{max}^{nujol}$ cm−1: 3280, 1570, 1380 |
| 22<br>(+)-isomer | 4-chlorophenyl | m.p. 163-164° C.*1<br>MS(m/z): 379(M+)<br>IR $\nu_{max}^{nujol}$ cm−1: 3250, 1710, 1700, 1330, 1150<br>$[\alpha]_D^{20}$ +53.8°<br>(c = 1.86, ethyl acetate)<br>Sodium salt: colorless powder<br>FABMS(m/z): 424, 402(M+ + 1)<br>IR $\nu_{max}^{nujol}$ cm−1: 1580, 1380<br>$[\alpha]_D^{20}$ +47.5°<br>(c = 1.03, methanol) |
| 23<br>(−)-isomer | 4-chlorophenyl | m.p. 162.5-164° C.*1<br>MS(m/z): 379(M+)<br>IR $\nu_{max}^{nujol}$ cm−1: 3250, 1710, 1700, 1330, 1150<br>$[\alpha]_D^{20}$ −53.9°<br>(c = 1.02, ethyl acetate)<br>Sodium salt: colorless powder<br>FABMS(m/z): 424, 402(M+ + 1)<br>IR $\nu_{max}^{nujol}$ cm−1: 1580, 1380<br>$[\alpha]_D^{20}$ −48.2°<br>(c = 0.906, methanol) |
| 24 | —CH₃ | m.p. 162.5-164° C.*2<br>MS(m/z): 283(M+)<br>IR $\nu_{max}^{nujol}$ cm−1: 3280, 1700, 1150<br>Sodium salt:<br>210-212° C.(dec.)*3<br>FABMS(m/z): 328, 306(M+ + 1)<br>IR $\nu_{max}^{nujol}$ cm−1: 3550, 1580 |
| 25 | —(CH₂)₃CH₃ | m.p. 128-129.5° C.*1<br>MS(m/z): 325(M+)<br>IR $\nu_{max}^{nujol}$ cm−1: 3290, 3250, 1700<br>Sodium salt:<br>188-190° C.(dec.)*3<br>FABMS(m/z): 370, 348(M+ + 1)<br>IR $\nu_{max}^{nujol}$ cm−1: 3260, 1560 |

*2 recrystallized from n-hexane, tetrahydrofuran and isopropyl ether
*3 recrystallized from water and isopropyl alcohol (same as in the following Examples)

TABLE 6

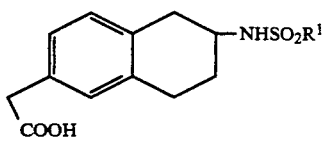

| Ex. No. | R¹ | Physical properties |
|---|---|---|
| 26 | 4-chlorophenyl | m.p. 130-133° C.*1<br>MS(m/z): 380(M+ + 1)<br>IR $\nu_{max}^{nujol}$ cm−1: 3320, 3150, 1710<br>Sodium salt: amorphous<br>FABMS(m/z): 424, 402(M+ + 1)<br>IR $\nu_{max}^{nujol}$ cm−1: 3260, 1570, 1385 |
| 27 | 4-methoxyphenyl | m.p. 121-123° C.*1<br>MS(m/z): 376(M+ + 1)<br>IR $\nu_{max}^{nujol}$ cm−1: 3320, 3250, 1720<br>Sodium salt:<br>m.p. 195-197° C.*3 |
| 28 | 2-naphthyl | m.p. 184-186° C.*1<br>MS(m/z): 396(M+ + 1)<br>IR $\nu_{max}^{nujol}$ cm−1: 3350, 3240, 1720<br>Sodium salt:<br>m.p. 137-144° C.*3 |
| 29 | 3-pyridyl | m.p. 174-177° C.*1<br>MS(m/z): 347(M+ + 1)<br>IR $\nu_{max}^{nujol}$ cm−1: 3300, 2500, 1710<br>Sodium salt:<br>m.p. 203-205° C.*3 |
| 30 | —CH₃ | m.p. 136.5-137.5° C.*1<br>MS(m/z): 283(M+ + 1)<br>IR $\nu_{max}^{nujol}$ cm−1: 3270, 1690<br>Sodium salt:<br>m.p. 267-269° C.(dec.)*3 |
| 31 | —(CH₂)₃CH₃ | m.p. 113-113.5° C.*1<br>FABMS(m/z): 326(M+ + 1)<br>IR $\nu_{max}^{nujol}$ cm−1: 3280, 1690<br>Sodium salt:<br>m.p. 208-210° C.*3 |

EXAMPLE 32

A mixture of 1.51 g of 6-(2-thienyl)sulfonylamino-5,6,7,8-tetrahydronaphthalene-2-acetic acid, 20 ml of methylene chloride, one drop of dimethylformamide and 3.3 ml of thionyl chloride is refluxed for 2 hours, and the solvent is removed to give yellow oil. A solution of the oil in 20 ml of methylene chloride is added dropwise to a solution of 1.30 g of methyl 4-aminobenzoate and 1.31 g of triethylamine in 15 ml of methylene chloride under stirring at room temperature. After the mixture is stirred overnight, the solvent is distilled off. Ethyl acetate and 10% hydrochloric acid are added to the residue, and the organic layer is separated therefrom, washed, dried and evaporated to remove the solvent. The resulting solid is recrystallized from a mixture of tetrahydrofuran and isopropyl ether to give 1.58 g of methyl 4-{[6-(2-thienyl)sulfonylamino-5,6,7,8-tetrahydronaphthalene-2-yl]acetylamino}benzoate as pale yellow crystals.

Yield 76%.
m.p. 210°-212° C.
FABMass(m/z): 485(M+ + 1).
IR$\nu_{max}^{nujol}$. (cm$^{-1}$): 3320, 3230, 1710, 1690, 1150.

EXAMPLES 33 TO 45

The corresponding starting compounds are treated in the same manner as described in Example 32 to give the compounds shown in Tables 7 to 8.

TABLE 7

[Structure: tetrahydronaphthalene with —NHSO$_2$R$^1$ and CONH(CH$_2$)$_q$CO$_2$CH$_3$ substituents]

| Ex. No. | R$^1$ | q | Physical properties |
|---|---|---|---|
| 33 | —C$_6$H$_4$—CH$_3$ | 2 | m.p. 131.5-132.5° C.*1 MS(m/z): 445(M+ + 1) IR $\nu_{max}^{nujol}$ cm−1: 3320, 3180, 1735, 1665, 1150 |
| 34 | —C$_6$H$_4$—Cl | 3 | m.p. 144-145° C.*4 MS(m/z): 479(M+ + 1) IR $\nu_{max}^{nujol}$ cm−1: 3340, 3160, 1730, 1660, 1160 |
| 35 | —C$_6$H$_4$—Cl | 2 | m.p. 170-171° C.*1 MS(m/z): 465(M+ + 1) IR $\nu_{max}^{nujol}$ cm−1: 3320, 3160, 1740, 1660, 1550 |
| 36 | —C$_6$H$_4$—Cl | 1 | m.p. 153-154° C.*4 MS(m/z): 450(M+) IR $\nu_{max}^{nujol}$ cm−1: 3350, 3180, 1750, 1660, 1160 |
| 37 | thienyl (S) | 3 | m.p. 105-107° C.*1 MS(m/z): 450(M+) IR $\nu_{max}^{nujol}$ cm−1: 3340, 3140, 1735, 1660, 1540 |
| 38 | —C$_6$H$_4$—Cl (+)-isomer | 3 | m.p. 111-113° C.*4 $[\alpha]_D^{20}$ +46.8°(c = 2.38, methanol) |
| 39 | —C$_6$H$_4$—Cl (−)-isomer | 3 | m.p. 110-112° C.*4 $[\alpha]_D^{20}$ −47.3°(c = 2.22, methanol) |

TABLE 7-continued

[Structure: tetrahydronaphthalene with —NHSO$_2$R$^1$ and CONH(CH$_2$)$_q$CO$_2$CH$_3$ substituents]

| Ex. No. | R$^1$ | q | Physical properties |
|---|---|---|---|
| 40 | —C$_6$H$_4$—Cl (+)-isomer | 2 | m.p. 132-134° C.*4 $[\alpha]_D^{20}$ +44.4°(c = 1.17, tetrahydrofuran) |
| 41 | —C$_6$H$_4$—Cl (−)-isomer | 2 | m.p. 132-133.5° C.*4 $[\alpha]_D^{20}$ −44.2°(c = 1.05, tetrahydrofuran) |

*4 recrystallized from ethyl acetate, isopropyl ether and n-hexane

TABLE 8

[Structure: tetrahydronaphthalene with —NHSO$_2$R$^1$ and CONH(CH$_2$)$_q$CO$_2$CH$_3$ substituents]

| Ex. No. | R$^1$ | q | Physical properties |
|---|---|---|---|
| 42 | —C$_6$H$_4$—OCH$_3$ | 2 | oil MS(m/z): 461(M+ + 1) IR $\nu_{max}^{neat}$ cm−1: 3280, 1735, 1650 |
| 43 | —C$_6$H$_4$—Cl | 3 | oil MS(m/z): 479(M+ + 1) IR $\nu_{max}^{neat}$ cm−1: 3380, 3280, 1735, 1650 |
| 44 | —CH$_3$ | 3 | m.p. 147.5-149.5° C.*5 MS(m/z): 382(M+) IR $\nu_{max}^{nujol}$ cm−1: 3280, 1715, 1650 |
| 45 | —(CH$_2$)$_3$CH$_3$ | 3 | m.p. 116-118° C.*5 FABMS(m/z): 425(M+ + 1) IR $\nu_{max}^{nujol}$ cm−1: 3350, 3180, 1740, 1650 |

*5 recrystallized from methanol-isopropyl ether (same as in the following Examples)

EXAMPLE 46

A mixture of 1.45 g of methyl 4-{[6-(2-thienyl)sulfonylamino-5,6,7,8-tetrahydronaphthalene-2-yl]acetylamino}benzoate, 10 ml of methanol, 9 ml of a 2N aqueous sodium hydroxide solution and 4 ml of tetrahydrofuran is stirred at room temperature overnight. Methanol and tetrahydrofuran are distilled off, and the residual mixture is washed and acidified. The precipitated crystals are collected by filtration, washed, dried and recrystallized from a mixture of tetrahydrofuran and isopropyl ether to give 1.33 g of 4-{[6-(2-thienyl)sulfonylamino-5,6,7,8-tetrahydronaphthalene-2-yl]acetylamino}benzoic acid as colorless crystals.

Yield 94%.

m.p. 250°-252° C.
FABMass(m/z): 471(M+ +1).
IR$\nu_{max}^{nujol}$(cm$^{-1}$): 3320, 3220, 1690, 1600.
Sodium salt: colorless crystals
m.p. 267°-269° C. (decomp.).
FABMass(m/z): 515, 493(M+ +1).
IR$\nu_{max}^{nujol}$(cm$^{-1}$): 1680, 1600.

EXAMPLES 47 to 59

The corresponding starting compounds are treated in the same manner as described in Example 46 to give the compounds shown in Tables 9 to 10.

TABLE 9

Structure: tetrahydronaphthalene with NHSO$_2$R$^1$ and CONH(CH$_2$)$_q$COOH substituents

| Ex. No. | R$^1$ | q | Physical properties |
|---|---|---|---|
| 47 | 4-CH$_3$-phenyl | 2 | m.p. 151-154° C.*1<br>MS(m/z): 431(M+ + 1)<br>IR $\nu_{max}^{nujol}$ cm-1: 3320, 3180, 1710, 1660<br>Sodium salt:<br>colorless powder<br>FABMS(m/z):<br>475, 453(M+ + 1)<br>IR $\nu_{max}^{nujol}$ cm-1: 3270, 1650, 1570, 1160 |
| 48 | 4-Cl-phenyl | 3 | m.p. 163.5-165° C.*6<br>MS(m/z): 465(M+ + 1)<br>IR $\nu_{max}^{nujol}$ cm-1: 3270, 1720, 1650<br>Sodium salt:<br>pale yellow powder<br>FABMS(m/z):<br>487(M+ + 1)<br>IR $\nu_{max}^{nujol}$ cm-1: 3270, 1630, 1560, 1150 |
| 49 | 4-Cl-phenyl | 2 | m.p. 171-172° C.*7<br>MS(m/z): 450(M+)<br>IR $\nu_{max}^{nujol}$ cm-1: 3350, 3160, 1705, 1655<br>Sodium salt:<br>colorless powder<br>FABMS(m/z):<br>495, 473(M+ + 1)<br>IR $\nu_{max}^{nujol}$ cm-1: 3260, 1640, 1570, 1460 |
| 50 | 4-Cl-phenyl | 1 | m.p. 191-193.5° C.*6<br>MS(m/z): 436(M+)<br>IR $\nu_{max}^{nujol}$ cm-1: 3330, 3160, 1720, 1660, 1150<br>Sodium salt:<br>colorless powder<br>FABMS(m/z):<br>481, 459(M+ + 1)<br>IR $\nu_{max}^{nujol}$ cm-1: 3280, 1600, 1160 |
| 51 | thienyl | 3 | m.p. 113-115° C.*7<br>MS(m/z): 436(M+)<br>IR $\nu_{max}^{nujol}$ cm-1: 3340, 3140, 1700, 1660<br>Sodium salt:<br>colorless powder<br>FABMS(m/z):<br>481, 459(M+ + 1)<br>IR $\nu_{max}^{nujol}$ cm-1: 3200, 1645, 1550, 1400 |

TABLE 9-continued

Structure: tetrahydronaphthalene with NHSO$_2$R$^1$ and CONH(CH$_2$)$_q$COOH substituents

| Ex. No. | R$^1$ | q | Physical properties |
|---|---|---|---|
| 52 | 4-Cl-phenyl (+)-isomer | 3 | m.p. 142-144° C.*6<br>[α]$_D^{20}$ +39.8°(c = 3.71, tetrahydrofuran)<br>Sodium salt:<br>colorless powder<br>[α]$_D^{20}$ +44.3°(c = 1.36, methanol) |
| 53 | 4-Cl-phenyl (−)-isomer | 3 | m.p. 143-144.5° C.*6<br>[α]$_D^{20}$ −40.5°(c = 2.42, tetrahydrofuran)<br>Sodium salt:<br>colorless powder<br>[α]$_D^{20}$ −45.1°(c = 1.02, methanol) |
| 54 | 4-Cl-phenyl (+)-isomer | 2 | m.p. 142.5-144° C.*7<br>[α]$_D^{20}$ +46.5°(c = 0.99, tetrahydrofuran)<br>Sodium salt:<br>colorless prisms<br>[α]$_D^{20}$ +43.0°(c = 2.72, methanol) |
| 55 | 4-Cl-phenyl (−)-isomer | 2 | m.p. 143-144.5° C.*7<br>[α]$_D^{20}$ −46.2°(c = 1.06, tetrahydrofuran)<br>Sodium salt:<br>colorless prisms<br>[α]$_D^{20}$ −42.7°(c = 2.67, methanol) |

*6 recrystallized from tetrahydrofuran-isopropyl ether
*7 recrystallized from ethyl acetate-isopropyl ether

TABLE 10

Structure: tetrahydronaphthalene with NHSO$_2$R$^1$ and CONH(CH$_2$)$_q$COOH substituents (different regiochemistry)

| Ex. No. | R$^1$ | q | Physical properties |
|---|---|---|---|
| 56 | 4-OCH$_3$-phenyl | 2 | oil<br>MS(m/z): 447(M+ + 1)<br>IR $\nu_{max}^{neat}$ cm-1: 3260, 1720, 1650<br>Sodium salt: amorphous<br>FABMS(m/z):<br>491, 469(M+ + 1)<br>IR $\nu_{max}^{nujol}$ cm-1: 3260, 1650, 1595, 1580, |
| 57 | 4-Cl-phenyl | 3 | oil<br>MS(m/z): 465(M+ + 1)<br>IR $\nu_{max}^{nujol}$ cm-1: 3270, 1720, 1650<br>Sodium salt: amorphous<br>FABMS(m/z):<br>509, 487(M+ + 1)<br>IR $\nu_{max}^{nujol}$ cm-1: 3260, 1650, 1560 |
| 58 | —CH$_3$ | 3 | m.p. 146-147.5° C.*5<br>IR $\nu_{max}^{nujol}$ cm-1: 3310, 3270, 1700, 1650<br>Sodium salt:<br>m.p. 210-212.5° C.*3 |

TABLE 10-continued

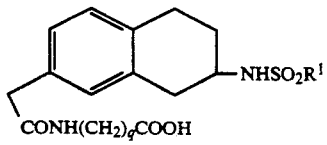

CONH(CH$_2$)$_q$COOH

| Ex. No. | R$^1$ | q | Physical properties |
|---|---|---|---|
| 59 | —(CH$_2$)$_3$CH$_3$ | 3 | m.p. 140–142° C.*8<br>MS(m/z): 410(M+)<br>IR $\nu_{max}^{nujol}$ cm$-$1: 3340, 3180, 1705, 1660, 1655<br>Sodium salt:<br>m.p. 204–208° C.*9 |

*8 recrystallized from ethyl acetate
*9 recrystallized from isopropyl ether, isopropyl alcohol and water

EXAMPLE 60

A mixture of 1.33 g of 7-(3-pyridyl)sulfonylamino-5,6,7,8-tetrahydronaphthalene-2-acetic acid, 20 ml of methylene chloride, 2 ml of thionyl chloride and one drop of dimethyformamide is srirred at room temperature for 30 minutes. After the solvent is distilled off, a solution of the resulting residue in 20 ml of methylene chloride is added to a mixture of 2.5 ml of a 30% aqueous dimethylamine solution and 20 ml of methylene chloride under cooling, and the mixture is stirred for one hour. The organic layer is separated from the mixture, washed, dried and evaporated to remove the solvent to give 785 mg of N,N-dimethyl-[7-(3-pyridyl)sulfonylamino-5,6,7,8-tetrahydronaphthalene-2-yl]acetamide as amorphous.

Yield 55%;
FABMass(m/z): 374(M+ +1);
IR$\nu_{max}^{nujol}$(cm$^{-1}$): 3140, 1735, 1630;

PREPARATION OF STARTING COMPOUNDS

PREPARATION 1

(1) A solution of 5.4 g of oxalyl chloride in methylene chloride is added dropwise to a suspension of 6.67 g of monoethylester of 1,4-phenylenediacetic acid in methylene chloride under cooling and stirring. After one drop of dimethylformamide is added to the mixture, the mixture is stirred at room temperature for 3 hours and evaporated to remove the solvent. A solution of resulting yellow oil in methylene chloride is added dropwise to a suspension of 12.8 g of alminum chloride in methylene chloride under stirring at 0° C., and the mixture is stirred for 10 minutes. After ethylene gas is flowed into the mixture for 30 minutes, the mixture is stirred at room temperature for 3 hours. Water and ethyl acetate are added to the mixture under cooling, and the organic layer is separated therefrom, washed, dried and evaporated to remove the solvent.

The resulting residue is purified by silica gel column chromatography to give 5.67 g of ethyl 6-oxo-5,6,7,8-tetrahydronaphthalene-2-acetate as colorless oil.

FABMass(m/z): 233(M+ +1);
IR$\nu_{max}^{neat}$(cm$^{-1}$): 1730–1720.

(2) A solution of 6.36 g of the product obtained above, 9.5 ml of pyridine and 4.33 g of methoxylamine hydrochloride in methanol is refluxed for 2.5 hours under argon. After the solvent is distilled off, ethyl acetate and 10% hydrochloric acid are added to the residue. The organic layer is separated from the mixture, washed, dried and evaporated to remove the solvent. The resiual oil is purified by silica gel column chromatography to give 5.37 g of ethyl 6-methoxyimino-5,6,7,8-tetrahydronaphthalene-2-acetate as pale yellow oil.

Mass(m/z): 261(M+).
IR$\nu_{max}^{neat}$(cm$^{-1}$): 1735, 1050.

(3) 216 mg of platinum oxide (IV) and 540 mg of oxalic acid are added to a solution of 1.57 g of the product obtained above in ethanol, and the mixture is subjected to catalytic hydrogenation under hydrogen gas atmosphere (2 to 3 atm) overnight. After a solution of hydrogen chloride in ethanol is added to the mixture, the catalyst is filtered off. After the solvent is distilled off, the residue is recrystallied from a mixture of ethanol and ether to give 772 mg of ethyl 6-amino-5,6,7,8-tetrahydronaphthalene-2-acetate hydrochloride as pale brown prism.

m.p. 217°–221° C. (decomp.).

PREPARATION 2

5.5 ml of 2M borane-methylsulfide complex in tetrahydrofuran are added to a solution of 1.31 g of ethyl 6-methoxyimino-5,6,7,8-tetrahydronaphthalene-2-acetate in tetrahydrofuran under argon at −5° to 0° C., and the mixture is stirred at room temperature overnight. Ethanol and 9% hydrogen chloride-ethanol are added to the mixture under cooing and stirring, and the mixture is stirred at room temperature for 30 minutes. After the solvent is distilled off, the residue is crystallized with a mixture of ethanol and ether to give 990 mg of 2-(6-amino-5,6,7,8-tetrahydronaphthalene-2-yl)ethanol hydrochloride as colorless solid.

m.p. 221°–224° C. (decomp.).

PREPARATION 3

(1) 110.52 g of trifluoroacetic anhydride are added dropwise to a solution of 76.29 g of DL-N-(methoxycarbonyl)aspartic acid in ethyl acetate under cooling. After the mixturte is stirred at room temperature for 2 hours, a part of solvent is distilled off. n-hexane is added to the solution slowly under cooling, and the precipitated crystals are collected by filteration to give 65.54 g of DL-N-(methoxycarbonyl)aspartic anhydride as colorless prism.

m.p. 102°–103° C.

(2) A mixture of 117.4 g of the product obtained above, 226.3 g of alminum chloride, 10.4 g of nitromethane and 270 g of benzene is refluxed for 3 hours. 10% hydrochloric acid is added to the reaction mixture, ethyl acetate and tetrahydrofuran are added thereto. The organic layer is separated from the mixture, dried and evaporated to remove the solvent. The residual solids, after the treatment of charcoal, are recrystallized from a mixture of ethyl acetate and n-hexane to give 147.9 g of 4-oxo-4-phenyl-2-methoxycarbonylaminobutyric acid as colorless prism.

m.p. 132°–135° C.

(3) A suspension of 25.12 g of the product obtained above, 52.5 ml of 2N hydrochloric acid and 2.60 g of palladium-carbon in tetrahydrofuran is subjected to catalytic hydrogenation under hydrogen gas atmosphere (4 atm) for 10 hours. After the reaction, the catalyst is filtered off, and a part of solvent is distilled off. Ethyl acetate is added to the solution, the solution is washed, dried and a part of solvent is distilled off. n-hexane is added to the mixture and the precipitated crystals are collected by filtration to give 22.07 g of 4-phenyl-2-methoxycarbonylaminobutyric acid as colorless needles.

m.p. 108.5°–110° C.

(4) A solution of 51.28 g of the product obtained above, 96.9 g of 2,2,2-trichloroethanol and 10.28 g of p-toluenesulfonic acid monohydrate in toluene is refluxed with Dean Strak apparatus for 5 hours. The reaction mixture is washed, dried and evaporated to remove the solvent, and the residue is distilled to give 71.5 g of 2,2,2-trichloroethyl 4-phenyl-2-methoxycarbonylaminobutyrate.

b.p. 90° to 95° C. (0.6 mmHg).

The product is allowed to stand to give colorless needles.

m.p. 31°–35° C.

(5) A solution of 1.77 g of ethyl 2-chloro-2-methylthioacetate in methylene chloride and a solution of 5.22 g of tin chloride (IV) in methylene chloride are added dropwise to 3.69 g of the product obtained above at the same time under cooling and stirring. After the mixture is stirred at room temperature for 2 hours, water, chloroform and then 10% hydrochloric acid are added thereto. The organic layer is separated from the mixture, dried and evaporated to remove the solvent. The residue is purified by silica gel column chromatography to give 4.37 g of ethyl 2-{4-[3-methoxycarbonylamino-3-(2,2,2-trichloroethoxycarbonyl)propyl]phenyl}-2-methylthioacetate as colorless oil.

IR$\nu_{max}^{neat}$(cm$^{-1}$): 3348, 1763, 1732.

(6) A mixture of 1.81 g of the product obtained above, 475 mg of zink powder and 15 ml of acetic acid is stirred at room temperature for 30 minutes, and then refluxed for one hour.

475 mg of zink powder are added to the mixture, and the mixture is refluxed for 1.5 hour. Further 950 mg of zink powder are added to the mixture and the mixture is refluxed for 2 hours. Insoluble materials are filtered off, and the filtrate are condensed. The residue is extracted with ethyl acetate, washed, dried and evaporated to remove the solvent. The residue is purified by silica gel column chromatography, and recrystallized from a mixture of ethyl acetate and n-hexane to give 956 mg of ethyl 4-(3-carboxy-3-methoxycarbonylaminopropyl)-phenylacetate.

m.p. 108°–110° C.

(7) A solution of 1.62 g of the product obtained above, 0.66 ml of oxalyl chloride and a catalytic amount of dimethylformamide in methylene chloride is stirred under cooling for 5 minutes and then at room temperature for 3 hours. 2.68 g of aluminum chloride are added to the mixture, and the mixture is stirred under cooling for one hour. Water and ethyl acetate are added to the mixture, and the organic layer is separated therefrom, washed, dried and evaporated to remove the solvent. The resulting oil is purified by silica gel column chromatography, and recrystallized from a mixture of ethyl acetate and n-hexane to give 983 mg of ethyl 8-oxo-7-methoxycarbonylamino-5,6,7,8-tetrahydronaphthalene-2-acetate as colorless needles.

m.p. 95°–97° C.

(8) A suspension of 0.92 g of the product obtained above, 60 mg of sodium borohydride in methanol is stirred under cooling for 10 minutes. After the solvent is distilled off, ethyl acetate and water are added thereto. The organic layer is separated from the mixture, washed, dried and evaporated to remove the solvent. The resulting crystals are recrystallized from a mixture of ethyl acetate and n-hexane to give 700 mg of ethyl 8-hydroxy-7-methoxycarbonylamino-5,6,7,8-tetrahydronaphthalene-2-acetate as colorless prism.

m.p. 99°–100.5° C.

(9) A suspension of 615 mg of the product obtained above, 180 mg of oxalic acid and 100 mg of 10% palladium-carbon in ethanol is subjected to catalytic hydrogenation under hydrogen gas atmosphere (4 atm) at 50° C. for 16 hours. The catalyst is filtered off, and the filtrate is condensed. Water is added to the residue and the solution is extracted with ethyl acetate, and the extract is washed, dried and evaporated to remove the solvent. The residue is recrystallized from a mixture of toluene and n-hexane to give 500 mg of ethyl 7-methoxycarbonylamino-5,6,7,8-tetrahydronaphthalene-2-acetate.

m.p. 89°–90° C.

(10) A solution of 586 mg of the product obtained above in 6N hydrochloric acid is refluxed for 13 hours. After the solvent is distilled off, 10% hydrogen chloride-methanol and methanol are added to the residue. The mixture is refluxed for 4 hours, and the solvent is distilled off. The residue is recrystallized from a mixture of methanol and ether to give 486 mg of metnyl 7-amino-5,6,7,8-tetrahydronaphthalene-2-acetate hydrochloride as colorless needles.

m.p. 158°–161.5° C.

Concomitantly, ethyl 8-oxo-7-methoxycarbonylamino-5,6,7,8-tetrahydronaphthalene-2-acetate is treated in the same manner as described in (9) to give ethyl 7-methoxycarbonylamino-5,6,7,8-tetrahydronaphthalene-2-acetate.

What is claimed is:

1. A tetrahydronaphthalene derivative of the formula:

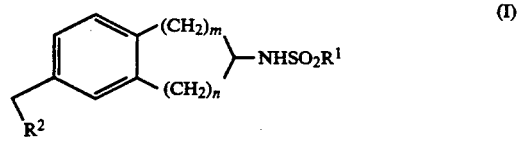

wherein $R^1$ is a phenyl group, a lower alkylphenyl group or a halogenophenyl group, and $R^2$ is a hydroxymethyl group, a carboxyl group, a lower alkoxycarbonyl group or a group of the formula:

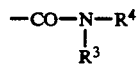

wherein $R^3$ is a hydrogen atom, $R^4$ is a lower alkoxycarbonyl-lower alkyl group or a carboxy-lower alkyl group, and m and n are different and are 1 or 2, or a pharmaceutically acceptable salt thereof.

2. The compound claimed in claim 1 in which $R^2$ is a hydroxymethyl group, a carboxyl group, or a group of the formula:

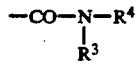

wherein $R^3$ is a hydrogen atom and $R^4$ is a carboxy-lower alkyl group.

3. The compound claimed in claim 1 in which m is 1 and n is 2.

4. The compound claimed in claim 2 in which m is 1 and n is 2.

5. The compound claimed in claim 4, in which $R^1$ is a phenyl group, a methylphenyl group or a chlorophenyl group, and $R^2$ is a carboxyl group or a group of the formula:

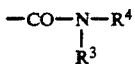

wherein $R^3$ is a hydrogen atom and $R^4$ is a carboxy-lower alkyl group.

6. The compound claimed in claim 5 in which $R^1$ is a chlorophenyl group, and $R^2$ is a group of the formula:

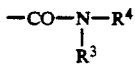

wherein $R^3$ is a hydrogen atom and $R^4$ is a carboxyethyl group or a carboxypropyl group.

7. The compound 4-{[6-(4-chlorophenyl)sulfonylamino-5,6,7,8-tetrahydronaphhtalene-2-yl]acetylamino}-n-butyric acid or a pharmaceutically acceptable salt thereof.

8. A pharmaceutical composition which is useful as a thromboxane $A_2$ antagonistic agent, the composition comprising a therapeutically effective amount of the compound claimed in claim 1 and a pharmaceutically acceptable carrier therefor.

9. A method for prophylaxis or treatment of a thrombotic disease in a warm-blooded animal which comprises administering to said warm-blooded animal an effective amount of the compound claimed in claim 1.

10. The compound 3-{[6-(4-chlorophenyl)sulfonylamino-5,6,7,8-tetrahydronaphthalene-2-yl]acetylamino}-n-propionic acid or a pharmaceutically acceptable salt thereof.

* * * * *